US006491803B1

(12) United States Patent
Shen et al.

(10) Patent No.: US 6,491,803 B1
(45) Date of Patent: Dec. 10, 2002

(54) TEST STRIP AND BIOSENSOR INCORPORATING WITH NANOMETER METAL PARTICLES

(75) Inventors: Thomas Y. S. Shen, Hsinchu (TW);
Wen-Chang Chen, Taipei (TW);
Hong-Ming Lin, Taipei (TW);
Jen-Hung Chuang, Taichung Hsien (TW)

(73) Assignee: Apex Biotechnology Corporation, Hsinchu (TW)

( * ) Notice: Subject to any disclaimer, the term of this patent is extended or adjusted under 35 U.S.C. 154(b) by 0 days.

(21) Appl. No.: 09/859,371

(22) Filed: May 18, 2001

(51) Int. Cl.[7] .................. G01N 27/327; B05D 3/00
(52) U.S. Cl. .............. 204/403.11; 204/403.06; 204/403.1; 204/403.01; 427/2.13
(58) Field of Search ............. 204/403, 403.01, 204/403.06, 403.1, 403.11; 427/2.13

(56) References Cited

U.S. PATENT DOCUMENTS 4,970,145 A * 11/1990 Bennetto et al. ............ 435/14
5,120,420 A    6/1992 Nankai et al.
5,160,418 A * 11/1992 Mullen ................... 204/403
5,508,171 A    4/1996 Walling et al.
5,727,548 A    3/1998 Hill et al.
5,762,770 A * 6/1998 Pritchard et al. .......... 204/403
5,770,028 A * 6/1998 Maley et al. .............. 204/435
5,997,817 A   12/1999 Crismore et al.

* cited by examiner

Primary Examiner—T. Tung
Assistant Examiner—Alex Noguerola
(74) Attorney, Agent, or Firm—Rothwell, Figg, Ernst & Manbeck (57) ABSTRACT

The present invention relates to a test strip and a biosensor having an increased conductivity and a slurry comprising a fiber, meal particles having a size in nanometer and a bioactive substance. The invention is characterized by incorporating metal particles having size in nanometer into the reaction layer of test strip and biosensor to increase the conductivity between the reaction layer and the electrodes so that the redox reaction can be readily completed and the measurement time can thus be shortened.

17 Claims, 6 Drawing Sheets

TEST STRIP AND BIOSENSOR INCORPORATING WITH NANOMETER METAL PARTICLES

BACKGROUND OF THE INVENTION

1. Field of the Invention

The present invention relates to a test strip and a biosensor having an increased conductivity with addition metal particles in nanometer size.

2. Description of the Prior Art

Various test strips, including electrochemical biosensor test strips, are used in measuring the amount of an analyte in a fluid. The biosensor test strips can provide rapid assays with a good accuracy so that they can be used in research and clinical field to treat a large number of samples.

U.S. Pat. No. 5,120,420 discloses a biochemical detecting electrode strip, including an electrode portion, an insulating layer, a reaction layer, and a sample receiving space which is formed by laying a resin board and a hydrophilic cover on the reaction layer. The biochemical detecting electrode strip has some disadvantages. Three steps are required in forming the reaction layer, i.e. forming the CMC layer to improve hydrophilic property of the carbon electrode surface, forming the GOD layer, and forming the conductive medium. Each step requires a subsequent drying step. The process is complicated. In addition, there is only one sampling inlet in the electrode strip and the sample is introduced into the reaction area through contacting with an electrode strip tip. Normally, the conductivity and its stability is not good because of the interference of the insulating materials in the test strip.

U.S. Pat. No. 5,508,171 relates generally to a determination of the concentration of analytes in fluids and more specifically to an amperometric biosensor for use in such determination. U.S. Pat. No. 5,727,548 relates to enzymatic sensor electrodes and their combination with reference electrodes to detect a compound in a liquid mixture. U.S. Pat. No. 5,997,817 discloses an improved electrochemical biosensor test strip for includes an indentation for tactile feel as to the location of the strips sample application port. However, there is a problem of poor conductivity and conductive stability caused by the interference materials occuring in the prior art.

There is a need to develop an electrode strip or a biosensor with a superior conductivity in the detection of biomolecules.

SUMMARY OF THE INVENTION

One object of the invention is to provide a test strip for detecting biochemical components in a sample, comprising:
an electrically insulating substrate;
a conducting film coated on one side of said insulting substrate to form an isolated and disconnected anode, and an isolated and disconnected cathode wherein said anode being disposed on the substrate, the anode being formed with, on both ends of the anode, a working electrode and an anode connector respectively; and said cathode disposed on the substrate, the cathode being formed with, on both ends of the cathode, a reference electrode and a cathode connector respectively;
a reaction layer wherein said layer is form by coating the working electrode and the reference elect with a slurry comprising a fiber, metal particles having a size in nanometer, and a bioactive substance; and
an electrically insulating layer disposed on the substrate and having an opening for receiving the sample on the reaction layer.

Another object of the invention is to provide a method of producing said test strip of the invention, which comprises the following steps:

(a) coating a conducting film on one side of an electric insulating substrate and forming isolated and disconnected an anode and a cathode;

(b) coating an electric insulating film on a part of the conducting film, wherein one end of an uncovered anode of the conducting film is at least a reference electrode and the other end an anode connector, and one end of an uncovered cathode of the conducting film is at least a working electrode and the other end a cathode connector; and (c) coating a region containing at least the working electrode, with a the slurry comprising a fiber, metal particles having a size in nanometer and a bioactive substance, and the reference electrode to form a reaction film so as to connect the working electrode and the reference electrode individually.

A further object of the invention is to provide a biosensor, which comprises a test strip of the invention and a detection device.

One object of the invention is to provide a slurry for increasing conductivity of a test strip, which comprises a fiber, a metal particle having a size in nanometer and a bioactive substance.

BRIEF DESCRIPTION OF THE ELEMENTS NUMERALS

1 Biosenor test strip
2 Electric insulating substrate
3 Cathode part
4 Working electrode Reaction film
5 Cathode Protection film
6 Anode part
7 Reference electrode
8 Anode connector
9 Reaction film
10 Electric insulating film
11 Opening
12 Opening end
13 Reticular covering layer
14 Protruding portion
a Inlet of first sample
b Inlet of second sample

DETAILED DESCRIPTION OF THE INVENTION

The present invention relates to a test strip and a biosensor containing a slurry comprising a fiber, metal particles having a size in nanometer and a bioactive substance. The invention is characterized by incorporating metal particles having a size in nanometer into the reaction layer of a test strip to increase the conductivity between the reaction layer and the electrodes so that the redox reaction can be readily completed and the measurement time can thus be shortened. Further, the reaction layer of the test strip is formed by coating the electrodes with the slurry in one step. Therefore, the process steps will be decreased and the costs will be reduced.

One object of the invention is to provide a test strip, which comprises:

an electrically insulating substrate;

a conducting film coated on one side of said insulting substrate to form an isolated and disconnected anode, and an isolated and disconnected cathode wherein said anode disposed on the substrate, the anode being formed with, on both ends of the anode, a working electrode and an anode connector respectively; and said cathode disposed on the substrate, the cathode being formed with, on both ends of the cathode, a reference electrode and a cathode connector respectively;

a reaction layer wherein said layer is formed by coating the working electrode and the reference electrode a slurry comprising a fiber, metal particles having a size in nanometer, and a bioactive substance; and an electrically insulating layer disposed on the substrate and having an opening for receiving the sample on the reaction layer.

According to the invention, the electric insulating substrate refers to a plate with a flat surface and an insulation property. Said substrate is selected from the group consisting of PVC, glass fiber, polyester sulphone, bakelite plate, PET, PC, glasss and ceramic board.

According to the invention, the conducting film is coated on one side of said insulting substrate to form an isolated and disconnected cathode and an isolated and disconnected anode. Preferably, the coating is achieved by screen printing with printing ink, or sticking with a metal film. More preferably, the metal film is selected from the group consisting of gold, silver, platinum and palladium. The printing ink is selected from the group consisting of carbon ink, gold ink, silver ink, a mixture of carbon and silver ink, volatile graphite, copper ink, or a mixture of the above (for example, printing it with silver ink first and then with carbon ink).

According to the invention, the cathode is partially covered by said electric insulating film and the uncovered ends of the cathode form a reference electrode and a cathode connector, respectively. The anode is also partially covered by said electric insulating film and the uncovered ends of the anode form a working electrode and an anode connector respectively. The reference electrode of the cathode is covered by the reaction film and cooperates together with the working electrode of the anode to detect the induced electric effect.

According to the invention, the reaction layer refers to a layer formed by coatings the working electrode and the reference electrode with the slurry of the invention. Preferably, the coating step comprises pipetting or screen printing. The screen printing is more preferred.

According to the invention, the slurry comprises a fiber, metal particles having a size in nanometer and a bioactive substance. The slurry is useful in increasing conductivity of a test strip. Normally, the biomolecule samples to be introduced in a test strip for detection have no conductivity. Such insulting molecules interfere the electrical conduction between the reaction layer and the electrodes and thus the conductivity of the test strip is poor. The above-mentioned problem can be solved by the addition of metal particles having a size in nanometer to the slurry for coating the electrodes.

According to the invention, the fiber refers to the ingredient for the preparation of the reaction layer of test strip. Any suitable fiber can be used. Preferably, said fiber is selected from the group consisting of cellulose, microcellulose, methylcellulose, carboxylmethyl-cellulose, starch, vinylalcohol, vinylpyrrolidone, PVA, PVP, PEG and gelatin. The particle size of said fiber ranges from 20–100 $\mu$m in diameter. The amount of said fiber is less than 40%.

According to the invention, the metal particle having a size in nanometer are suitable in the increase the conductivity of the reaction layer of a test strip. The metal particles are preferably selected from the group consisting of Fe Co, Cu, Ag, Au, Ni, Pd, Pt and the mixture, alloys, or nanocomposites containing these nanometer metal particles thereof. More preferably, the size of said metal particles ranges from 1–100 nm in diameter. The amount of said metal particle is less than 3%.

According to the invention, the bioactive substance refers to a substance for use in carrying out a biochemical or chemical reaction. Preferably, the bioactive substance is selected from the group consisting of enzyme, antigen, antibody, microorganism, animal cell, plant cell, and animal or plant tissue with components having biological recognition ability. More preferably, the bioactive substance is an immobilized enzyme. Most preferably, the bioactive substance is glucose oxidase.

According to the invention, the slurry optionally further comprises electrical mediator, polymer, salt, surfactant and water. The electrical mediator is preferably potassium ferricyanide. The surfactant is preferably selected from the group consisting of the surfactant such as Triton X-100, Triton X-405, Triton X-114, sodium lauryl sulfate, polyoxyethylenesorbitan monolaurate (Tween 20, Tween 40, Tween 60, Tween 80), and other water-soluble surfactant or detergent. The polymer is preferably selected from the group consisting of polyvinyl alcohol, polyvinyl pyrrolidone, polyethylene glycol, gelatin and the mixture thereof.

According to the invention, the electric insulating film is coated on one surface of said electric insulating substrate but does not cover the above-mentioned cathode connector, anode connector, working electrode and reference electrode. The region uncovered by the electric insulating film (including the working electrode and the reference electrode) forms a reaction region, which is then coated by the reaction film for testing samples.

According to the invention, the test strip further comprises a reticular covering layer. The reticular covering layer is made of a hydrophilic reticular material or a hydrophobic reticular material or metal wire mesh. The screen of the mesh is, but not limited to, 60 to 300 screens. The reticular covering layer is disposed on a sample inlet for producing capillary attraction between the reticular covering layer and the reaction layer. The reticular covering layer and a resulting capillary attraction facilitate sampling when a sample is introduced from an opening end on a side of the biosensor.

Another object of the invention is to provide a method of producing the test strip, which comprises the following steps:

(a) coating a conducting film on one side of an electric insulating substrate and forming isolated and disconnected an anode and a cathode;

(b) coating an electric insulating film on a part of the conducting film, wherein one end of an uncovered anode of the conducting film is at least a reference electrode and the other end an anode connector, ant one end of an uncovered cathode of the conducting film is at least a working electrode and the other end a cat ode connector; and (c) coating a region containing at least the working electrode, with a the slurry comprising a fiber, metal particles having a size in nanometer and a bioactive substance, and the reference electrode to form a reaction film so as to connect the working electrode and the reference electrode individually.

According to the invention, the slurry is coated by pipetting or screen printing. The screen printing is more preferred.

A further object of the invention is to provide a biosensor, which comprises a test strip as described herein and a detection device. Preferably, the detection device is an amperometric sensor Another further object of the invention is to provide a slurry for increasing conductivity of a test strip, which comprises a fiber, metal particles having a size in nanometer and a bioactive substance.

The test strip of the present invention does not require several drying steps and forms a uniform and flat reaction layer on a surface. Therefore, biosensors can be produced in a more convenient way, an analyst can be sampled in a more convenient and effective way, the inconvenience and of a patient can be reduced to a minimum. Meanwhile, an accurate detection result can be obtained. Moreover, the test strip of the invention has multiple sampling sites and superior conductivity. The way of sampling can be achieved by dropping a sample on the test strip, or approaching the test strip to a sample. Given the above, the test strip and biosensor of the invention can easily and accurately detect and process a number of samples.

DETAILED DESCRIPTIONS OF PREFERRED EMBODIMENT OF THE INVENTION

Figure 3:
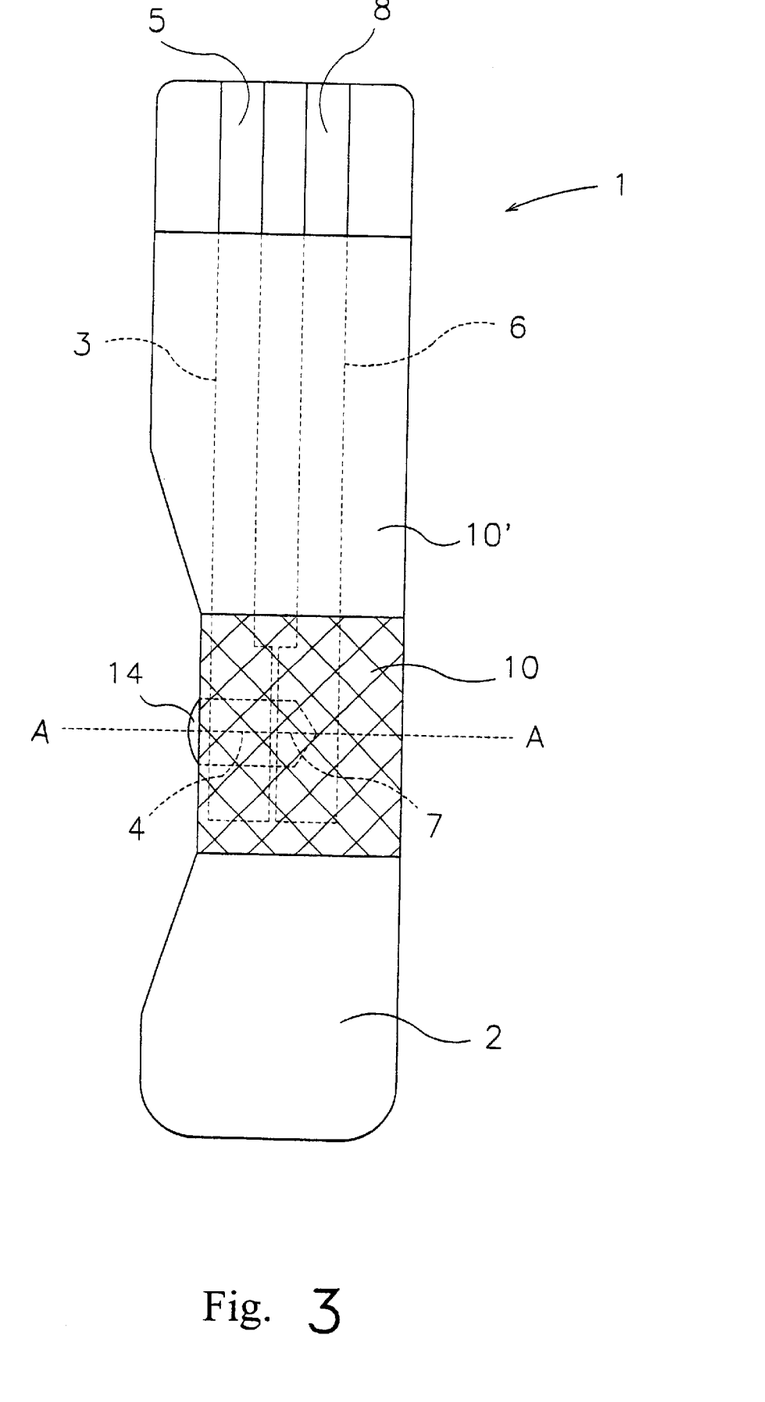
FIG. 3 is a top view of the test strip of FIG. 1.

With reference to FIGS. 1 to 4, a test strip 1 according to an embodiment of the invention for detecting biochemical components in a sample includes: an electrical insulating substrate 2; an cathode 3 disposed on the substrate 2, the cathode 3 provided with working electrodes 4 (as shown in FIG. 3) and an cathode connector 5 at both ends of the cathode 3 respectively; and an anode 6 disposed on the substrate 2, wherein the anode is provided with a reference electrode 7 (as shown in FIG. 3) and an anode connector 8 at both ends of the anode 6, respectively.

Figure 1:
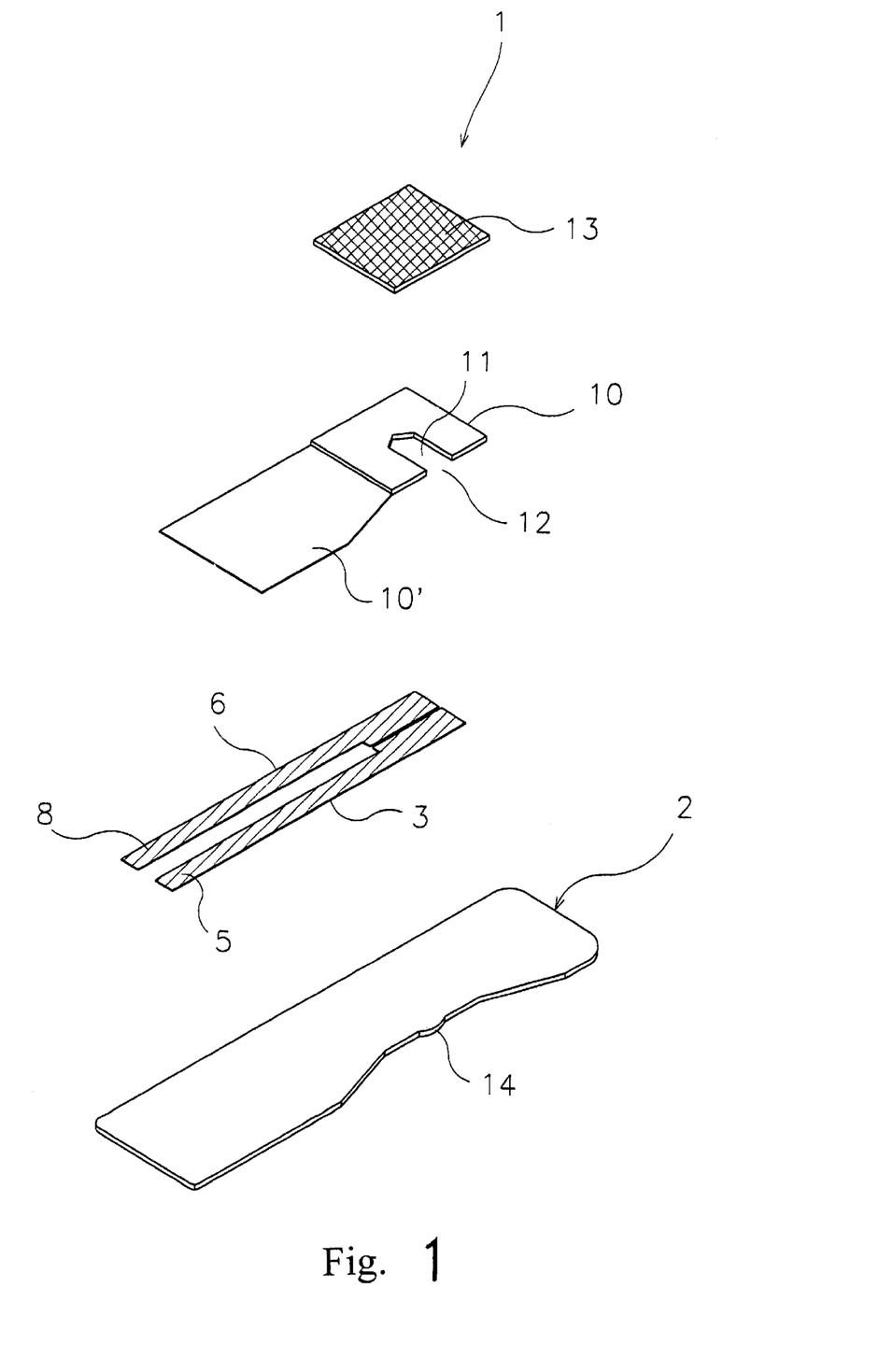
FIG. 1 is an exploded view of the test strip according to an embodiment of the invention.
Figure 2:
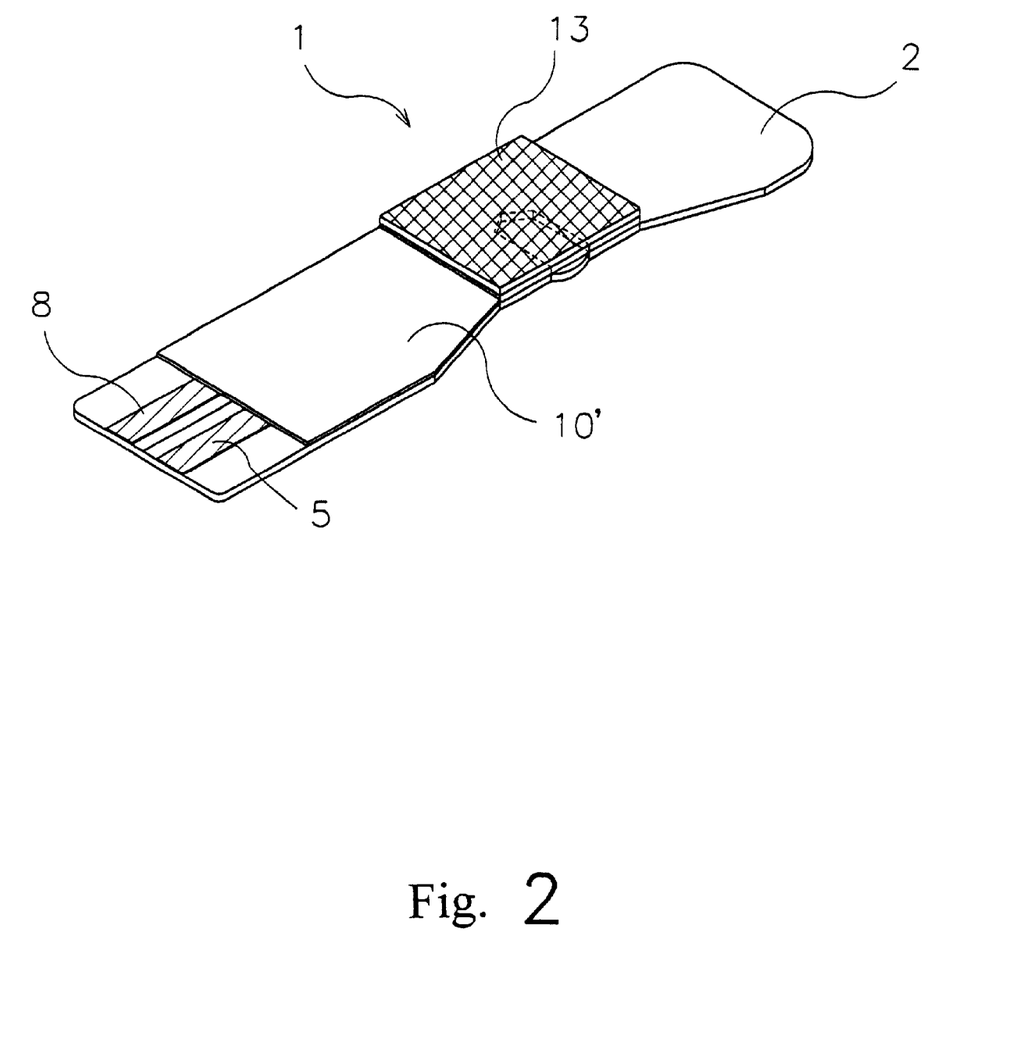
FIG. 2 is perspective view of the test strip of FIG. 1.

The substrate 2 is electrically insulated and has a flat surface. The substrate 2 should be thermally resistant under temperatures ranging from 40° C. to 200° C. in a thermal process, which is useful for increasing conductance and adherence of the cathode 3 and anode 6.

The cathode 3 and the anode 6 are made of two spaced-apart conductive films 2, 2' to be connected to a detection device (not shown in the figures).

Figure 4:
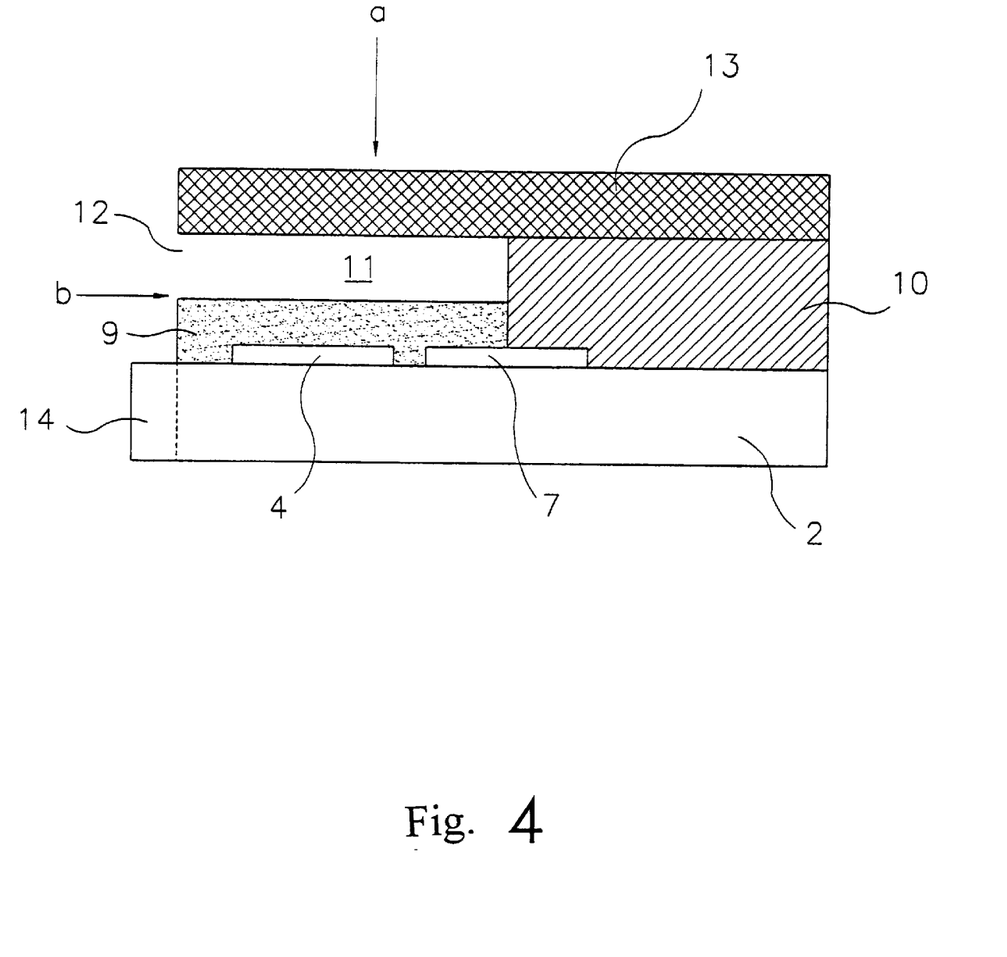
FIG. 4 is a sectional view of the biosensor taken from line A—A of FIG. 3.

After partially covered by the electrical insulating layers 3 and 3', the anode 6 is formed with, at both exposed ends of the anode, an anode connector 8 for connecting the detection equipment and a working electrode 4 on which a bioactive layer is disposed, i.e. a reaction layer 9 (see FIG. 4). The working electrode 4 is used for transmitting electrical signals induced by chemical or biochemical reactions of the sample to the detection device. The electric insulating layers 3 and 3' are covered, and the cathode 3 is formed with, respectively on both exposed ends, a cathode connector 5 for connecting the detection device and the reference electrode 7 (please refer to FIG. 3) on which a reaction layer 9 is disposed. The reference electrode 7 is used in cooperation with the wording electrode 4 for detecting the electrical signals from the samples.

The test strip 1 of the invention further comprises a reaction layer 9 on the working electrode 4 and the reference electrode 7 The reaction layer 9 is a bioactive layer and is used for contacting the sample to produce chemical reactions. The reaction layer 9 does not overlap the electric insulating layer 10.

The reaction layer 9 is formed by disposing a slurry of the invention of bioactive substances on a part of the substrate 2, the anode 3 and the cathode 6.

The test strip 1 of the present invention comprises electric insulating layers 3 and 3' on the substrate 2, which has an opening 11 (with a height of about 0.25 to 0.3 mm) for receiving the sample in the reaction layer 9, and an opening end 12.

A reaction area for receiving the sample to react refers to an area confined by the opening 11 and the reaction layer 9 which is under the opening 11. The thickness of the electric insulating layer 10 above the reaction area is generally in range from 0.25 mm to 0.3 mm.

The test strip 1 of the invention further comprises the reticular covering layer 13 for protecting the reaction layer 9 and for increasing capillarity with the sample on the electrically insulating layer 10. The reticular covering layer 13 covers at least a part of the opening 11. A sample can be received on the reaction layer 9 from the opening end 12 by the capillary attraction between the reticular covering layer 13 and the reaction layer 9. When the reticular covering layer 13 is made of a hydrophilic reticular material, a hydrophilic sample can be introduced from the opening end 12, or from above the reticular covering layer in the direction 'a' of FIG. 4. When the reticular covering layer 3 is made of a hydrophobic reticular material, a hydrophilic sample, having a less affinity, is introduced from the opening end 12 through capillarity.

In the test strip 1 of the invention, a sample is introduced to the reaction layer 9 in two ways. When the reticular covering layer 13 is hydrophilic, the sample can be introduced in a first sample introduction direction 'a' of FIG. 4 by a hydrophilic attraction provided by the hydrophilic reticular covering layer 13. Alternatively, a sample can be introduced from a second sample introduction direction 'b' of FIG. 4 by a capillary attraction. In the direction 'b', the biosensor 1 can be directly approached to a patient to obtain a sample and the sample can be rapidly and sweepingly attracted to the reaction layer 9. Not only the detection can be improved, but also the sample demands can be reduced. Furthermore, when the reticular covering layer 13 is hydrophobic, a sample can be introduced in the second sample introduction direction 'b' into the reaction layer 9. This is done by approaching the biosensor 1 to a patient. For example, the patient's ear is pierced by a lancet to produce a blood droplet and then the biosensor 1 is approached to the blood droplet which is to be introduced to the reaction layer 9 in the second sample introduction direction 'b'. Thus, the sample demands can be reduced as low as possible.

For example, the patient's ear is pierced by a lancet to produce a blood droplet and then the biosensor 1 is approached to the blood droplet which is to be introduced to the reaction layer 9 in the second sample introduction direction 'b'. Thus, the sample demands can be reduced as low as possible.

In a preferred embodiment, the substrate 2 of the test strip 1 further has a semicircular protruding port on 14 under the opening end 12 to serve as a sample contact point. The semicircular protruding portion 14 allows the biosensor 1 to get closer to a sampled point to facilitate sampling, and lessen patient's sense (when the biosensor contacts the patient).

The process of producing the electrode test strip of the biosensor of the invention is simplified and the quality of the strip is improved. The production steps are summarized as follows.

Step 1

A layer of conducting film 2, 2' which includes an cathode 3 and a anode 6 is printed on any one flat surface of a flat plate substrate 2 by screen printing. The conducting film is made of conductive ink which is suitable for screen printing, such as carbon ink, silver irks gold ink, a combination of silver and carbon inks, or any combination of these inks. For example, it is printed with silver ink and then with carbon ink. The conducting film is then dried at a temperature of 40° C. to 150° C.

Step 2

A 0.25 to 0.30 mm thick electric insulating layer 3' is disposed by film pasting technology on the side on which the conducting film is printed. The electric insulating layer 3 in a thickness of 0.25 to 0.3 mm, which has an opening 11 and an opening end 12, is disposed on the reaction area. The working electrode 4 and the reference electrode 7 are formed by keeping the conducting film partly exposed. The electrodes 4 and 7 are restricted in an area confined by the opening 11. The area formed by the working electrode 4 and the reference electrode 7 is referred to herein a reaction area.

Step 3

Bioactive substances are dropped or printed on the reaction area and dried at a temperature of 10° C. to 60° C. to form a reaction layer 9.

Step 4

A reticular covering layer 13 is disposed on the reaction layer 9.

EXAMPLES

The present invention is described in detail in accordance with the following embodiments.

Example 1

A conducting film 2, 2' of carbon ink was screen printed on a flat surface of a PC board substrate to form an anode and a cathode which were independently isolated. The substrate was dried at a temperature of 130° C. Then, the PET electric insulating layer 3 in a thickness of 0.27 mm was disposed on the same side of the flat surface with the conducting film 2, 2' to form an anode connector 6, a cathode connector 7, a working electrode 8 and a reference electrode 9 by keeping the conducting film partly exposed. The area formed by the working electrode and the reference electrode refers to the reaction area 5.

| | |
|---|---|
| glucose oxidase | 3% |
| potassium ferricyanide | 20% |
| methyl cellulose | 2% |
| Cellulose | 25% |
| Triton X-100 (t-Octylphenoxypolyethanol) | 1% |
| Glutamic acid | 1% |
| Metal particle having size of nanometer | 1% |
| Phosphate buffer (pH = 6.5) | 47% |

The bioactive substances of the above formula were added on the reaction area. The test strip was dried at a temperature of 50° C. for 15 minutes. Then, a reticular covering layer (Teterlon, T120-54) was disposed on the reaction film and the current electrode test strip of the biosensor was obtained.

Figure 6:
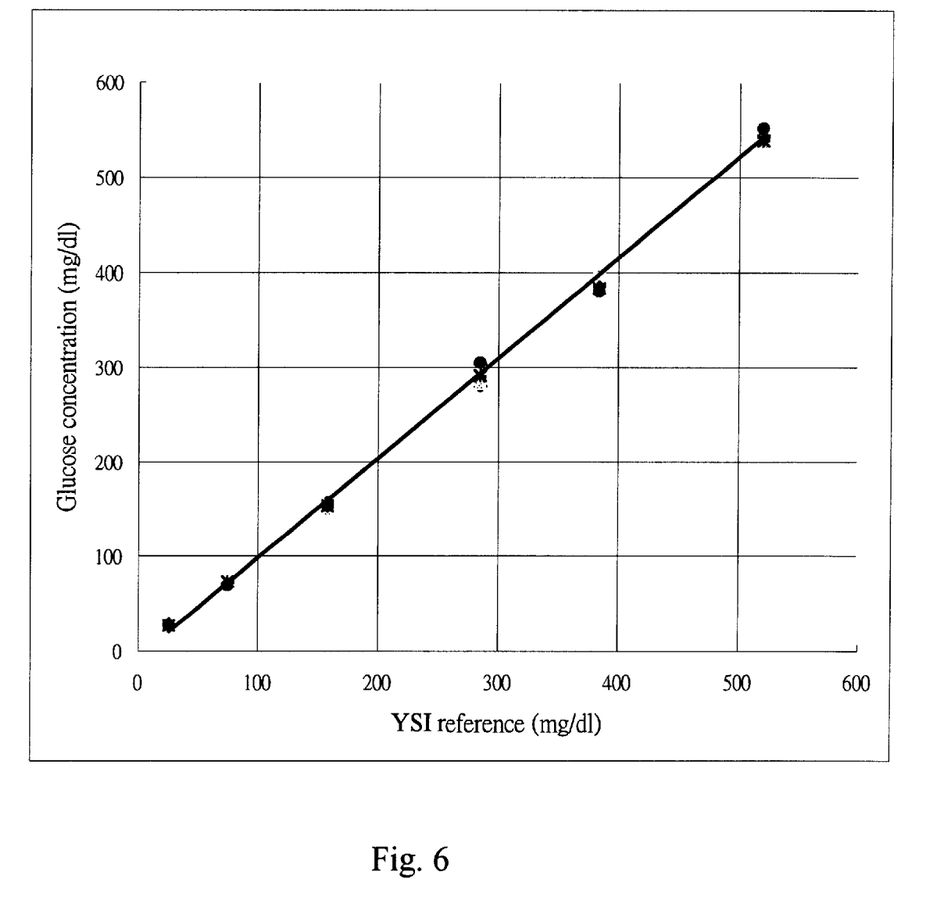
FIG. 6 is a comparison chart of the blood glucose concentrations measured by using the test strip and biosensor according to the invention, and by a YSI glucose analyzer.

A disposable current electrode test strip was thus produced for detecting the blood sugar by taking whole blood as a sample The results are shown in FIG. 6, a comparison chart of blood sugar concentrations measured by the biosensor according to the invention and by a YSI blood sugar analyzer. The results showed that the measurement performed by the biosensor according to the present invention was accurate.

Example 2

The procedures used in Example 2 are analogus to those used in Example 1, except that the formula is as follows:

| | |
|---|---|
| glucose oxidase | 3% |
| potassium ferricyanide | 20% |
| methyl cellulose | 1.5% |
| Cellulose | 25% |
| Triton X-100 (t-Octylphenoxypolyethanol) | 1% |
| Glutamic acid | 1% |
| Metal particle having size of nanometer | 2.5% |
| Phosphate buffer (pH = 7.0) | 46% |

Example 3

The procedures used in Example 3 are analogus to those used in Example 1, except that the formula is as follows:

| | |
|---|---|
| glucose oxidase | 3% |
| potassium ferricyanide | 20% |
| methyl cellulose | 1.5% |
| Cellulose | 20% |
| Triton X-100 (t-Octylphenoxypolyethanol) | 1% |
| Glutamic acid | 1% |
| Metal particle having size of nanometer | 1.5% |
| Phosphate buffer (pH = 6.5) | 52% |

Example 4

The procedures used in Example 4 are analogus to those used in Example 1, except that the formula is as follows:

| | |
|---|---|
| glucose oxidase | 3% |
| potassium ferricyanide | 20% |
| methyl cellulose | 1.5% |
| Cellulose | 20% |
| Triton X-100 (t-Octylphenoxypolyethanol) | 1% |
| Glutamic acid | 1% |
| Metal particle having size of nanometer | 0.1% |
| Phosphate buffer (pH = 6.5) | 54.4% |

Example 5

The procedures used in Example 5 are analogus to those used in Example 1, except that the reticular covering layer is replaced with a hydrophobic polyester PES-37T. The production steps are the same as those illustrated in Example 1. After a reaction layer was formed, the reticular material PES-37T was pasted on the electrical insulating layer and a test strip was obtained.

Example 6

The procedures used in Example 6 are analogus those used in Example 1, except that the reticular covering layer is replaced with a stainless wire mesh (100–300 mesh). The production steps are the same as those illustrated in Example 1. After a reaction layer was formed, the stainless wire mesh was pasted on the electrically insulating layer and a test strip was obtained.

Example 7

The procedures used in Example 7 are analogus to those used in Example 1, except that the covering layer is replaced with a hydrophobic reticular polyester PES-42T. The production steps are the same as those illustrated in Example 1. After a reaction layer was formed, the reticular PES-42T was pasted on the electrically insulating layer and a test strip was obtained.

Example 8

The procedures used in Example 8 are analogus to those used in Example 1, except that the reticular covering layer is replaced with a hydrophobic reticular material PET-43T. The PET-43T was soaked and processed by 1% of Triton X-100 to become hydrophilic. The production steps are the same as those illustrated in Example 1. After a reaction layer was formed, the reticular material PET-43 T was pasted on the electrically insulating layer and a test strip was obtained.

The disclosed biosensor of the present invention not only includes the advantages of simplicity in production and accuracy in detection, but also includes multiple sampling sites. Samples can be dropped to release, or the biosensor can be approached to a patient to take samples for facilitating sampling. A sample can be easily and rapidly introduced to the reaction layer. Furthermore, the pains of a patient can be lessened by reducing sample demands. This invention provides a convenient and effective solution for manufacturers, analysts and patients.

Example 9

Figure 5:
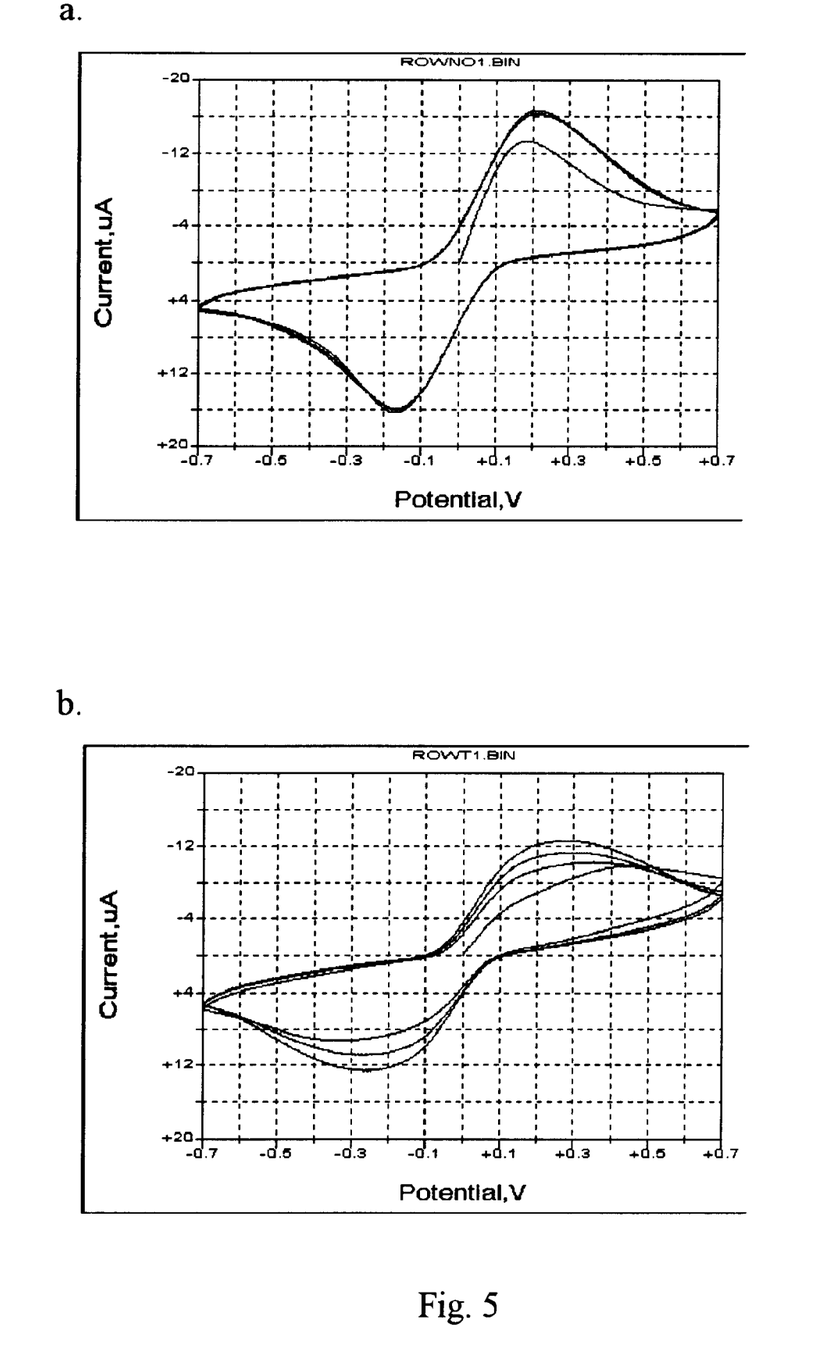
FIG. 5 is a plot of the test of cyclic voltammograms showing the effect of modifying slurry with metal particles having a size in nanometer to their response of water test. A, metal particles modified slurry; B, unmodified.

A test of cyclic voltammograms was carried out to show the effect of modifying slurry with metal particles having a size in nanometer to their response of water test. As shown in FIG. 5, the reaction current of the test strip with metal particles having a size in nanometer was more stable without any change within the reaction time (see FIG. 5A). On the country, the reaction current of the test strip without metal particles having a size in nanometer was changed within the reaction time (see FIG. 5B). The addition of metal particles having a size in nanometer can stabilize the conductivity of the conductive medium in the test strip. Further, the redox reaction in the test strip with metal particles having a size in nanometer could be occurred evenly and quickly. The conductibility of the electron was thus increased. The above test results suggest that the addition of the metal particles having a size in nanometer can improve the accuracy and precision of the test strip.

The methods and features of this invention have been sufficiently described in the above examples and descriptions. It should be understood that any modifications or changes without departing from the spirits of the invention are intended to be covered in the protection scopes of the invention.

What is claimed is:

1. A test strip, which comprises:
    an electrically insulating substrate;
    a conducting film coated on one side of said insulating substrate to form an isolated and disconnected anode, and an isolated and disconnected cathode wherein said anode is disposed on the substrate, the anode being formed with, on both ends of the anode, a working electrode and an anode connector respectively; and said cathode is disposed on the substrate, the cathode being formed with, on both ends of the cathode, a reference electrode and a cathode connector respectively;
    a reaction layer wherein said layer is formed by coating the working electrode and the reference electrode with a slurry comprising a fiber, metal particles having a size in nanometer, and a bioactive substance, potassium ferricyanide as electrical mediator, a polymer and a surfactant; and
    an electrically insulating layer disposed on the substrate and having an opening for receiving the sample on the reaction layer.

2. The test strip of claim 1, wherein said substrate is selected from the group consisting of PVC, glass fiber, polyester suphone, bakelite plate, PET, PC, glass and ceramic board.

3. The test strip of claim 2, wherein the particle size of said fiber ranges from 20–100 μm in diameter.

4. The test strip of claim 1, wherein said fiber is selected from the group consisting of cellulose, microcellulose, methylcellulose, carboxylmethyl-cellulose, starch, vinylalcohol, vinylpyrrolidone, PVA, PVP, PEG and gelatin.

5. The test strip of claim 1, wherein said metal particles are selected from the group consisting of Fe, Co, Cu, Ag, Au, Ni, Pd, Pt and the mixture, alloys, or nanocomposites containing these nanometer metal particles thereof.

6. The test strip of claim 5, wherein the size of said metal particles ranges from 1–100 nm in diameter.

7. The test strip of claim 1, wherein said bioactive material is selected from the group consisting of enzyme, antigen, antibody, microorganism, animal cell, plant cell, animal or plant tissue with the component having biological recognition ability.

8. The test strip of claim 7, wherein said bioactive material is an enzyme.

9. The test strip of claim 8, wherein said enzyme is an immobilized enzyme.

10. The test strip of claim 8, wherein said enzyme is glucose oxidase.

11. The test strip of claim 1, wherein said slurry further comprises a salt and water.

12. The test strip of claim 11, wherein the electrical mediator is a potassium ferricyanide.

13. The test strip of claim 1, wherein the polymer is selected from the group consisting of polyvinyl alcohol, polyvinyl pyrrolidone, polyethylene glycol, gelatin and the mixture thereof.

14. The test strip of claim 1, wherein the surfactant is selected from the group consisting of Triton X-100, Triton C-405, Triton X-114, sodium lauryl sulfate, polyoxyethylenesorbitan monolaurate (Tween 20), Tween 40, Tween 60, Tween 80, or other water-soluble surfactant or detergent.

15. A method of producing said test strip of claim 14, which comprises the following steps:
    (a) coating a conducting film on one side of an electric insulating substrate and forming isolated and disconnected an anode and a cathode;

(b) coating an electric insulating film on a part of the conducting film, wherein one end of an uncovered anode of the conducting film is at least a reference electrode and the other end an anode connector, and one end of an uncovered cathode of the conducting fit is at least a working electrode and the other end a cathode connector; and (c) coating a region containing at least the working electrode, with a the slurry comprising a fiber, metal particles having a size in nanometer and a bioactive substance, and the reference electrode to form a reaction film so as to connect the working electrode and the reference electrode individually.

16. A biosensor, which comprises the test strip of claim 1 and a detection device.

17. The biosensor of claim 16, wherein the detection device is an amperometric sensor.

* * * * *